(12) United States Patent
Levieux et al.

(10) Patent No.: US 9,308,029 B2
(45) Date of Patent: Apr. 12, 2016

(54) BONE CLAMPING SYSTEM

(71) Applicants: Jerome Levieux, Geneva (CH); Guillaume Amblard, Geneva (CH)

(72) Inventors: Jerome Levieux, Geneva (CH); Guillaume Amblard, Geneva (CH)

(73) Assignee: SPINEART SA, Meyrin (CH)

( * ) Notice: Subject to any disclaimer, the term of this patent is extended or adjusted under 35 U.S.C. 154(b) by 0 days.

(21) Appl. No.: 14/363,505

(22) PCT Filed: Dec. 7, 2012

(86) PCT No.: PCT/EP2012/074859
§ 371 (c)(1),
(2) Date: Jun. 6, 2014

(87) PCT Pub. No.: WO2013/083811
PCT Pub. Date: Jun. 13, 2013

(65) Prior Publication Data
US 2014/0324103 A1  Oct. 30, 2014

(30) Foreign Application Priority Data

Dec. 9, 2011 (FR) ...................................... 11 61386

(51) Int. Cl.
*A61B 17/70* (2006.01)

(52) U.S. Cl.
CPC ......... *A61B 17/7068* (2013.01); *A61B 17/7047* (2013.01)

(58) Field of Classification Search
CPC ........... A61B 17/7062; A61B 17/7065; A61B 17/7067; A61B 17/7068; A61B 17/7071; A61B 17/7047; A61B 17/7059
USPC ................................................... 606/249–279
See application file for complete search history.

(56) References Cited

U.S. PATENT DOCUMENTS

| | | | |
|---|---|---|---|
| 5,928,231 A * | 7/1999 | Klein et al. ..................... 606/60 |
| 8,343,190 B1 * | 1/2013 | Mueller ............. A61B 17/7068 606/248 |
| 2006/0247640 A1 | 11/2006 | Blackwell et al. |
| 2008/0177391 A1 * | 7/2008 | Mitchell ............ A61B 17/7065 623/17.16 |
| 2008/0183211 A1 | 7/2008 | Lamborne et al. |
| 2008/0183218 A1 * | 7/2008 | Mueller ............. A61B 17/7068 606/280 |
| 2011/0054531 A1 * | 3/2011 | Lamborne .......... A61B 17/7068 606/249 |
| 2011/0066186 A1 * | 3/2011 | Boyer et al. ................... 606/249 |
| 2011/0284208 A1 * | 11/2011 | MacLeod et al. ............ 166/88.2 |
| 2012/0136390 A1 * | 5/2012 | Butler ................ A61B 17/7067 606/248 |
| 2012/0150228 A1 * | 6/2012 | Zappacosta ........ A61B 17/7068 606/248 |
| 2013/0072979 A1 * | 3/2013 | Butler ................ A61B 17/7068 606/248 |
| 2013/0184753 A1 * | 7/2013 | Keiper ............... A61B 17/7047 606/248 |

OTHER PUBLICATIONS

International Search Report, dated Feb. 8, 2013, from corresponding PCT application.

\* cited by examiner

*Primary Examiner* — Jerry Cumberledge
*Assistant Examiner* — Tessa Matthews
(74) *Attorney, Agent, or Firm* — Young & Thompson

(57) ABSTRACT

A bone clamping system includes a shaft (3), a first plate (1) integrally attached to the shaft and a second, movable plate (20), wherein a locking leaf (22, 23), penetrating into the shaft (3) or not, locks the second plate (20) on the shaft (3).

11 Claims, 6 Drawing Sheets

BONE CLAMPING SYSTEM

Figure 1:
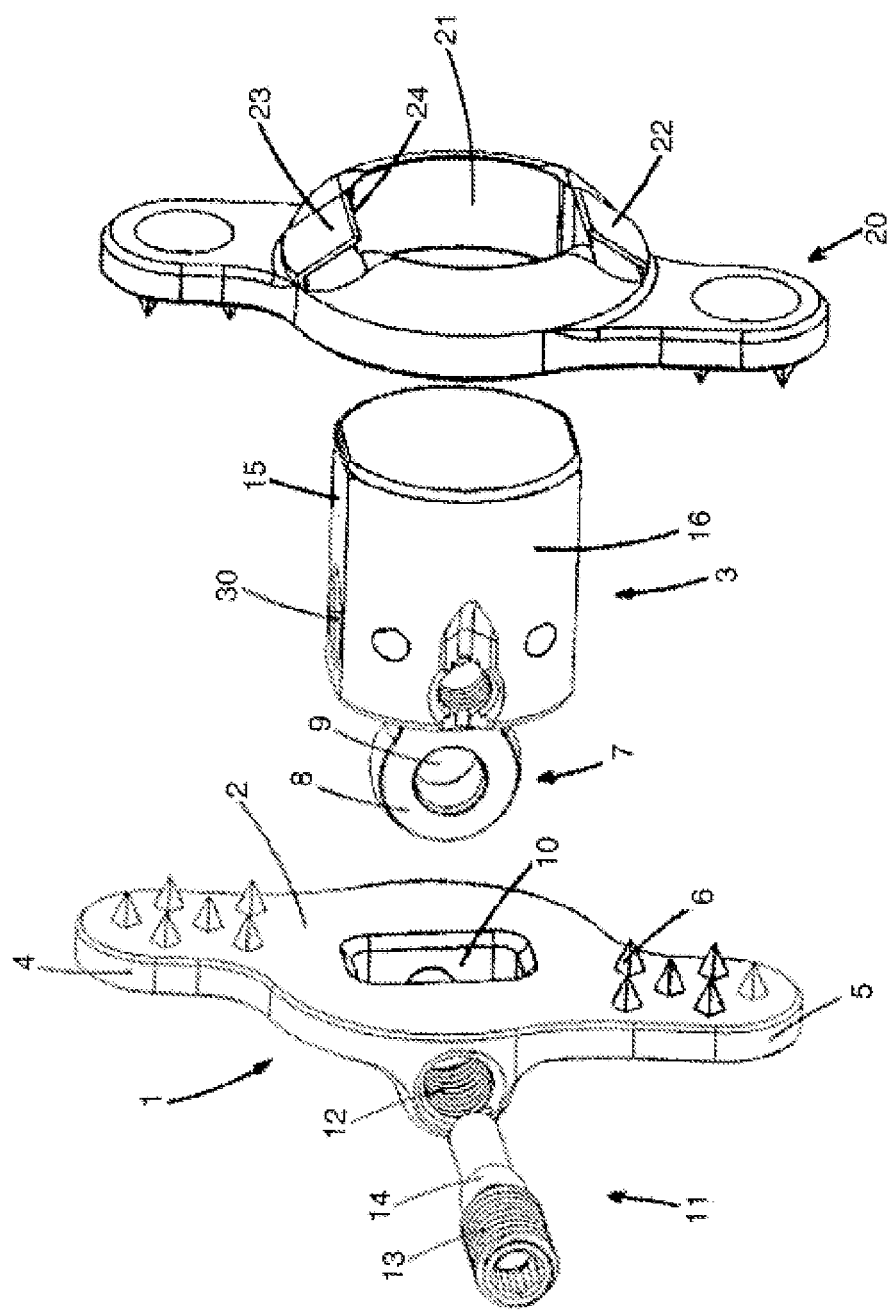

The present invention relates to a bone-clamping system, especially for posterior osteosynthesis of the spine, and to the uses thereof.

Diseases of the spine are treated in various ways. Arthrodesis may be one of the therapeutic options chosen and involves blocking adjacent vertebrae at one or more levels. There are several types of implantable devices with which it is possible to obtain osseous fusion of the vertebrae by a posterior approach. The types of device mainly used are screws introduced into the pedicles and connected to each other by rigid plates or bars which have the ability to correct deformations of the spine (sagittal and/or lateral curvature) and to suppress the mobility of the vertebrae in relation to each other so as to obtain osseous fusion.

A more recent alternative to this solution is the use of a posterior osteosynthesis device placed between the spinous processes, which fixes the vertebrae in relation to each other while maintaining a desired space. The surgery then poses less risk, since it does not require any work in the dangerous areas near the dura mater or the nerve roots.

There are interspinous fusion devices permitting the immobilization of one or more segments of the spine and their realignment. These devices generally comprise two plates facing each other, and a central joining element arranged between these plates and allowing these plates to be locked in a position compressed against the spinous processes, as described in US20080183211.

Some devices are locked in situ either by means of a set screw, as described in US 2008/0183211, or by means of a ratchet having a series of grooves on the transverse body connecting the plates to each other, and one or more teeth on the movable plate capable of moving in translation along said transverse body described in US20110066186.

However, the set screw does not permit reliable locking of the device, and the operating surgeon has to perform an additional step in order to be certain of effective locking. Moreover, this manipulation may be difficult for one operating surgeon to do on his own, and an assistant is needed in order to keep the device compressed and at the same time to lock the set screw.

The ratchet by definition imposes certain positions on the plate that is movable in translation. These positions correspond to the increment (or step) of the grooves on the transverse body. This is also a costly solution in terms of its manufacture. Finally, this solution may provide quite low performance on account of the necessary miniaturization of the design.

Furthermore, US2008177391 describes an implantable spacer system for implantation between adjacent spinous processes. The system comprises a shaft and two wings. A spacer is engaged on the shaft and is blocked by the wings. A first wing is installed at one end of the shaft, and the second wing uses a washer which is blocked in a groove in order to assume a unique and well-defined position. The spacers limit the movement of extension of two adjacent spinous processes by resisting the compression forces that are applied to the spacer by the adjacent spinous processes. The spacer limits the movement in order to limit the collapse of the foraminal canal within which the nerves are disposed. Once assembled, the implant comprises two wings arranged on both ends of the spacers. The wings resist undesired movement and maintain the location of the spacers between adjacent spinous processes.

It would therefore be desirable to overcome the disadvantages of the bone-clamping systems by implementing a solution which automatically locks the implant without a supplementary step and without the need for verification and does so irreversibly, which locks the implant in any position continuously and without increment, which locks the implant with a heightened performance level (resistance to detachment), and which is more economical than the machining of a ratchet.

Moreover, some devices have an articulation of one or more plates for better adaptation to the anatomical variation of the spinous processes. This articulation is more particularly present on an axle, such as a pivot, making it possible to compensate solely for the variations in the thickness of the spinous processes, as described in US 2011/0066186.

However, such a solution has disadvantages. The variations in the shape and thickness of the spinous processes are not located in a single plane, and a connection of the pivot type proves inadequate for optimal contact of the implant with the faces of the spinous processes.

It would therefore be desirable to overcome these advantages by implementing a solution which permits the rotation of one of the plates in all directions, preferably with great amplitude, and which permits maximum adaptation to the anatomical variations, which may be considerable. The contact thus obtained would be more congruent and would then promote the mutual immobilization of the vertebrae and long-term bone fusion.

In addition, some devices of the prior art are able to contain bone graft situated directly in contact with the spinous processes. The central element connecting the two plates thus has a through-opening, but the latter is obstructed by the locking system of the plates for keeping them in position as described in US 2011/0066186.

However, to ensure that the bone graft plays an active part in the fusion of the bone elements, it has to be continuous and of a sufficient volume. In the case where this volume is reduced and obstructed by a component element of the device, the role of the graft may be compromised. Moreover, the presence of a graft around the element for locking the implant, for example a ratchet system, may compromise the locking function, since the teeth may be impeded.

It would therefore be desirable to have a large volume available for the bone graft, without discontinuity, and preferably outside the area permitting the locking of the implant, such that the graft cannot interfere with the technical elements.

Moreover, some devices have to be assembled either before the implantation of the device, as described in US 2011/0066186, or during the implantation of the device, as described in US 2008/0183211.

However, the number of manipulations and the operating time are considerable, as is the risk of error during the assembly. Consequently, the risk of contaminating the device also increases.

It would therefore also be desirable to have available a pre-assembled device.

In summary, it would therefore be desirable to have available an interspinous fusion device which in particular is pre-assembled, provides continuous and automatic locking, and permits minimally invasive and rapid surgery.

For other orthopedic uses, it would also be desirable to have available a device which in particular is pre-assembled, provides continuous and automatic locking, and permits minimally invasive and rapid surgery.

After extensive research, the applicant has developed a novel device which provides complete satisfaction and is based on a continuous self-blocking system. Moreover, if so desired, a chamber allows the surgeon to install a bone graft.

The novel device comprises a shaft, a first plate rigidly fixed to the shaft, and a second, movable plate in which a unidirectional locking with blades, penetrating or not penetrating into the shaft, blocks the second plate on the shaft, preventing the plates from moving away from each other. Depending on the relative hardness of the blade and of the shaft, the blade penetrates into the shaft or remains at the surface.

As will be seen herein below, the shaft constitutes a continuous self-blocking system during a movement of the second plate toward the first plate.

It is for this reason that the present application relates to a bone-clamping system, especially for spinous processes, characterized in that it comprises a first plate and a second plate, which are installed face to face, and an optionally tubular shaft, which is installed approximately perpendicularly with respect to the two plates and passes at least partially through one of them, the plates comprising an inner face and an outer face, in that a surface of the inner face of the plates is preferably provided with raised roughening features, in that the first plate is movable relative to the second plate, in that the first plate is fixed in translation with respect to the shaft, and in that the shaft and the second plate form a non-return mechanism, without pawl, comprising a flexible resilient blade which is installed on the second plate and forms an angle of 10 to 90° with respect to the axis of the shaft, an end edge of said flexible resilient blade coming to bear against a smooth surface of the shaft, the end edge of said flexible resilient blade coming to bear against a smooth surface of the shaft being sharp, the system also being characterized in that the material of the flexible resilient blade is of a hardness identical to or harder than the material of the smooth surface of the shaft, such that the coming together of the plates is irreversible without an external aid, as a consequence of which bone elements can be effectively clamped between the two plates.

It should be noted that, in the present application, the indefinite article must conventionally be considered as a generic plural (meaning "at least one" or else "one or more"), except when the context shows the contrary (1 or "a single"). Thus, for example, when it is stated above that the non-return mechanism comprises a flexible blade installed on the second plate, this denotes the presence of one or more flexible blades.

The first plate, fixed in translation with respect to the shaft, can be made in one piece with the axle. However, under preferred conditions of use of the invention, the first plate and the shaft are two separate components. In particular, these two separate components are coupled in order to allow the articulation of the first plate with respect to the shaft. Since the spinous processes can be of any shape, it is in fact desirable that one plate, preferably the first plate, can tilt at an angle with respect to the shaft.

Advantageously, when the first plate and the shaft are two separate components, one of the ends of the shaft comprises a circular hole arranged diametrically with respect to the axis of the shaft, for example with an annular shape.

The first plate can then comprise a cavity for the passage of this end, and a means used as an axis for the circular hole in order to allow the shaft to move around a fixed point. The means can in particular be a screw, a peg, a pin, or a partially threaded pin. If its diameter is smaller than that of the radial circular hole, the first plate can move in a limited manner in a diametric direction of the shaft, around a fixed point situated in the axis of this means. Thus, the first plate can tilt at an angle with respect to the shaft, and the clamping system for spinous processes can adapt to spinous processes of varied shapes. The first plate and the second plate are therefore not systematically parallel.

For certain uses such as the fixation of spinous processes, the plates are elongate plates, thus having a length and a width. The width is a mean width if not substantially constant. For other uses such as consolidation of a fracture of a limb or the closure of an osseous flap of the cranium, the plates can be circular plates.

The means used as an axis for the circular opening, to allow the shaft to move around a fixed point, can in particular be a screw comprising a ball installed facing the cavity of the first plate. The ball can then have a diameter scarcely less than that of the aforementioned radial circular hole.

The second plate can move in translation along the axis of the shaft and approach the first plate and form a kind of vise. The second plate has a well permitting the passage of the shaft and allowing the plates to come together.

The shaft and the second plate form a non-return mechanism such that the coming-together of the plates is irreversible without an external aid. This mechanism prevents the retreat of the second plate when the latter comes toward the first plate. By virtue of the absence of a pawl mechanism imposing an increment, the coming-together of the plates has the advantage of being able to be continuous.

The shaft can be smooth only at the location where the flexible blade bears on it. Under preferred conditions of use of the invention, the shaft is a smooth rod across more than 50%, especially across more than 60%, particularly across more than 70%, very particularly across more than 80% of its surface.

The material of the flexible blade is of a hardness that is identical to or harder than the material of the smooth surface of the shaft on which it comes to bear. Thus, by bearing on the shaft, the sharp end edge of the flexible blade embeds itself in the shaft. The inclination of the blade with respect to the axis of the shaft has the effect that the coming-together of the plates is irreversible. In the case where the materials of the flexible blade and of the smooth surface of the shaft are identical, the geometry of the sharp end edge of the flexible blade and the inclination of the latter with respect to the smooth surface of the shaft play an important role in the principle of irreversible continuous locking, the penetration of the flexible blade being less, possibly zero, but being compensated by the inclination. The shaft can therefore be smooth only at the location where the flexible blade bears on it. Under preferred conditions of use of the invention, more than 50% of the volume of the shaft, especially more than 60%, particularly more than 70%, very particularly the entirety of the shaft, is made of material that is less hard than the material of the flexible blade, which simplifies manufacture.

Thus, by virtue of the inclination of the flexible resilient blade with respect to the axis of the shaft, the sharp end edge of the flexible blade moves away from the axis when the plates come together, and the sharp end edge embeds itself or fixes itself in the shaft when the movement stops. Movement in the opposite direction becomes impossible under normal conditions of use. The sharp end edge embeds itself in the shaft especially as the difference in hardness increases and/or the force tending to move the plates away from each other increases.

The inclination of a flexible resilient blade with respect to the general plane of the second plate is, for example, 10 to 90°, especially 15 to 80°, preferably 15 to 60°, more particularly 20 to 50°, and very particularly 25 to 40°. Indeed, when a flexible resilient blade is not adequately inclined, the blocking effect may not take place, since the blade is able to slide on the shaft. The more the inclination of the flexible resilient blade approaches the vertical to the axis) (90°), the more preferable is the presence of an abutment for preventing the return of the blade under the action of a force tending to move the plates away from each other.

When the flexible resilient blade is not plane, for example arched, the angle considered is the tangent to the blade upon contact with the shaft.

The shaft can have any cross section, for example circular, but this cross section is advantageously non-circular, for example an oval or a rounded rectangle (rectangle whose short sides are replaced by half-circles or arcs of a circle of the same radii, and whose short sides and long sides are replaced by half-circles or arcs of a circle with different radii between the short and long sides). Depending on the use, a circular or non-circular cross section will be preferred.

A "smooth" surface of the shaft against which said flexible resilient blade comes to bear is intended to signify that the surface can be smooth or finely striated or can have a roughened surface state (surface more or less unpolished) or can have longitudinal grooves, so as not to create a notch effect and to permit continuous blocking. The geometry and nature of the surfaces of the shaft against which said flexible resilient blade comes to bear are designed to increase the attachment of the one or more blades with maximum speed and performance in order to resist loads that tend to cause the second plate to retreat.

Under other preferred conditions of use of the invention, in combination with the preceding ones, the second plate comprises one or more flexible resilient blades, preferably two flexible blades. These two flexible blades are preferably provided on each side of the location of the shaft. Advantageously, the edge of said one or more flexible blades has a series of notches or teeth allowing the sharp end edge to more easily embed itself in the shaft and increase the attachment against the shaft with more speed.

In yet other preferred conditions of use of the invention, in combination with the preceding ones, an abutment is provided facing the one or more blades, in order to reinforce the action of the blades.

Under further preferred conditions of use of the invention, in combination with the preceding ones, for some uses the shaft is provided with one or more recesses in order to receive a bone graft. This opening can be in particular a multiplicity of openings close together like a honeycomb for example, or a single opening.

Under other preferred conditions of use of the invention, in combination with the preceding ones, a surface of the inner face of the plates is provided with raised roughening features for certain applications such as clamping of spinous processes.

The movement of the second plate is advantageously guided along the shaft by a non-circular shape, for example an oval or rounded rectangle shape, of the cross section of the shaft, and the well permitting the passage of the shaft then has a complementary shape.

The shaft is advantageously made of polyether ether ketone (PEEK) or of another material having the same mechanical and radio transparent properties, so as to permit visualization of a graft during radiography checks. However, it can also be made of other implantable polymer materials or metals, for example titanium, alloyed or pure.

The flexible resilient blade and preferably the entirety of the shaft will be able to be made of other implantable polymer materials or metals, for example titanium, alloyed or pure. The material of the flexible resilient blade has a hardness identical to or preferably harder than the material of the smooth surface of the shaft on which it bears.

When the flexible resilient blade bears on a curved surface, the corresponding radius of a section of the shaft will for example be, depending on the application, from 4 to 180, preferably from 40 to 160, especially from 50 to 150, very particularly from 60 to 140 mm. The large radii are better suited for systems providing a volume for placement of a bone graft such as the systems for gripping spinous processes. For uses that do not require the provision of a free volume in the shaft, such as the consolidation of the fracture of a limb or the closure of a cranial bone flap, the corresponding diameter of a section of the shaft like a rod will be, for example, from 1 to 30, preferably from 1.5 to 15, especially from 3 to 10, very particularly from 4 to 8 mm.

The thickness of the shaft, if it is the smallest dimension of the section between the bearing surfaces of the blades, will be, for example, from 0.5 to 30 mm, very particularly from 5 to 20 mm. For uses that do not require the provision of a free volume in the shaft, the thickness of the shaft will be, for example, from 0.5 to 30, preferably from 1 to 20, especially from 2 to 12, very particularly from 4 to 8 mm.

The length of the shaft will be, for example, from 10 to 50, preferably from 15 to 45, especially from 20 to 40, very particularly from 25 to 35 mm.

The length of the elongate plates will be, for example, from 1.5 to 8, preferably from 2 to 7, especially from 2 to 6, very particularly from 3 to 5 cm.

The maximum width of the plates will be, for example, from 3 to 25, preferably from 4 to 15, especially from 5 to 12, very particularly from 6 to 10 mm.

The thickness of the plates will be, for example, from 1 to 8, preferably from 1.5 to 6, especially from 1.5 to 4, very particularly from 2 to 3 mm.

The plates have substantially the same shape, as is shown herein below in the figures.

The length of the well excluding the plate will be, for example, from 2 to 14, preferably from 3 to 12, especially from 4 to 10, very particularly from 6 to 8 mm.

The number of the blades will advantageously be from 1 to 8, preferably from 1 to 4, especially 2.

The systems used for gripping bones, especially spinous processes, and forming the subject matter of the present invention have very advantageous properties and qualities. They may generally serve as bone grips for creating a point of fixation to another device or for joining two or more bone elements.

In the case of spinous processes, they make it possible to easily block the relative movement of the vertebrae concerned.

In the case of articular facets, they make it possible to easily block the relative movement of the adjacent vertebrae.

They can be used to constitute, for example, a fixation or anchoring point for another device on a spinous process or transverse process or a lamina of the posterior arch.

The elastic blades ensure the irreversibility of the movement by automatically locking the position of the plates and maintaining the compression on the bone.

"Automatically" means that the blocking takes place without the operating surgeon acting on the blocking system itself.

An important advantage of this system is the ease of its installation, and also its stability over time, obtained by virtue of the non-return mechanism. It is fitted in place by a single tightening maneuver, with just one hand being needed. Moreover, there is no risk of a blocking screw coming loose over time, which is important because this type of device is designed to be implanted for a lifetime. The tightening is regulated continuously, in contrast to a pawl mechanism.

These qualities are illustrated hereinafter. They justify the use of the above-described bone-gripping systems especially
- in the stabilization of the vertebral column,
- in osteosynthesis procedures, for example consolidation of the fracture of a limb or the resolution of a mechanical disorder on the skeleton,
- in the closure of a cranial bone flap.

It is for this reason that the present application also relates to a method for stabilizing the vertebral column, in which bone-gripping systems as described above are installed on adjacent vertebrae, and said adjacent vertebrae are blocked. Preferably, a bone graft is also installed in the one or more recesses of the shaft.

The present application also relates to a method for consolidating a bone fracture or fissure in which
- bone-clamping systems as described above are installed on bone fragments, especially fragments of flat bones such as the cranium, scapula or sternum, and
- the bone fragments are then clamped between the first plate and second plate of a bone-clamping system as described above.

The present application also relates to a method for consolidating a bone fracture or fissure in which
- the bone is drilled,
- bone-clamping systems as described above are installed by introducing the shaft into the drilled hole, and
- the bone elements are then clamped between the first plate and second plate of a bone-clamping system as described above. This method is particularly suitable for cases of transverse, spiral or oblique fracture or fissure.

The bones concerned by the above methods are, for example, fragments of flat bones, such as the cranium, scapula or sternum, short and round bones, such as the carpal bones, or long and round bones, such as the radius, the tibia or the fibula.

The present application also relates to a method for closing a cranial bone flap in which
- a bone-clamping system as described above is installed on the cranial bone in question, for example the frontal bone or the parietal bone, and
- the cranial bone in question is then clamped between the first plate and second plate of a bone-clamping system as described above.

In this case, in order to clamp the bone elements that are to be immobilized, the shaft passes through the bone wall at the site of cuts, usually without the need for supplementary drilling.

For surgical use, the present application also relates to said sterile devices, especially packed in a package preserving their sterility.

The preferred conditions of use of the above-described clamping systems for spinous processes also apply to the other subjects of the invention mentioned above, especially to the procedures and methods using them and for their manufacture.

The present application finally relates to a method for clamping and coupling objects, which are preferably osseous, characterized in that a system is made available which comprises a first plate and a second plate which are installed face to face, and an optionally tubular shaft which is installed approximately perpendicularly with respect to the two plates and passes at least partially through one of them, the plates comprising an inner face and an outer face, a surface of the inner face of the plates being preferably provided with a raised roughening, in that the first plate is movable relative to the second plate, in that the first plate is fixed in translation with respect to the shaft, and in that the shaft and the second plate form a non-return mechanism, without pawl, comprising a flexible resilient blade which is installed on the second plate, an end edge of said flexible resilient blade bearing against a smooth surface of the shaft and forming an angle of 10 to 90° with respect to the axis of the shaft, the end edge of said flexible resilient blade bearing against a smooth surface of the shaft being sharp, the system also being characterized in that the material of the flexible blade is of a hardness identical to or harder than the material of the smooth surface of the shaft, such that the coming together of the plates is irreversible without an external aid,
- one or preferably two separate objects are provided,
- the one or more objects are placed between the plates installed face to face, especially opposite the raised roughening, and
- the continuous moving-together of the first plate relative to the second plate is effected in order to clamp the one or more objects.

The invention overcomes many disadvantages of the prior art by using a solution which in particular:
- automatically locks the device without a supplementary step and without the need for verification and does so irreversibly,
- locks the device in any position continuously and without increment,
- locks the device with a heightened performance level (resistance to detachment),
- is more economical than the machining of a rack.

In addition, the device according to the invention permits, on some models, the rotation of one of the plates in all directions with great amplitude, by means of a connection, especially of the spherical type, and permits maximum adaptation to the anatomical variations, which may be considerable. The contact thus obtained is also congruent and promotes the mutual immobilization of the vertebrae and long-term bone fusion.

The device according to the invention also permits, if so desired, a large volume for a bone graft, without discontinuity, and outside the area permitting the locking of the implant, such that the graft cannot interfere with the technical elements.

With a device according to the invention, the operating time is reduced to the maximum extent and the risk of error during assembly is eliminated. Moreover, manipulation is possible without contact with the implant, thereby reducing the risk of contamination of the device.

The preferred conditions of use of the systems for gripping spinous processes, as described above, apply also to the other subjects of the invention set out above, especially to the procedures and methods using them.

Figure 2:
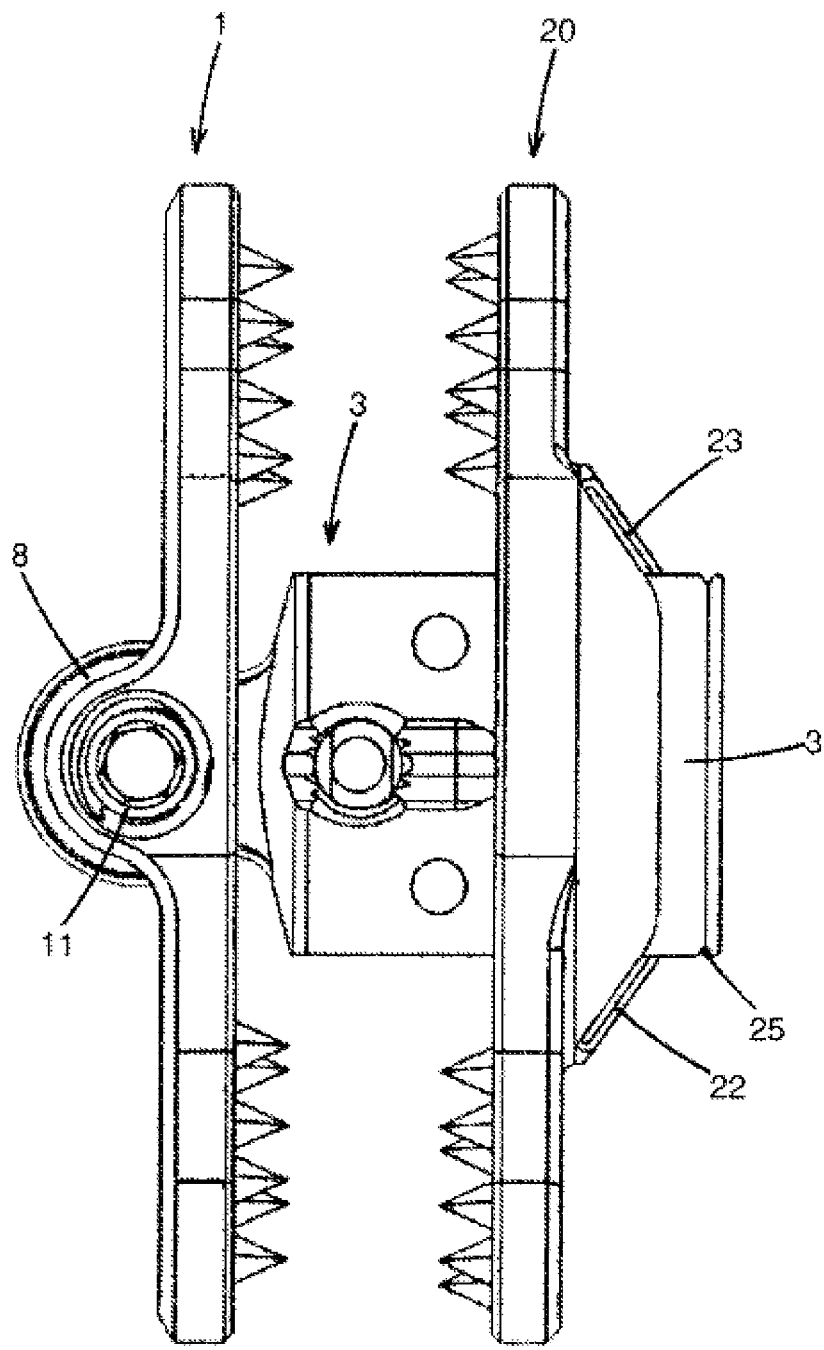
Figure 3:
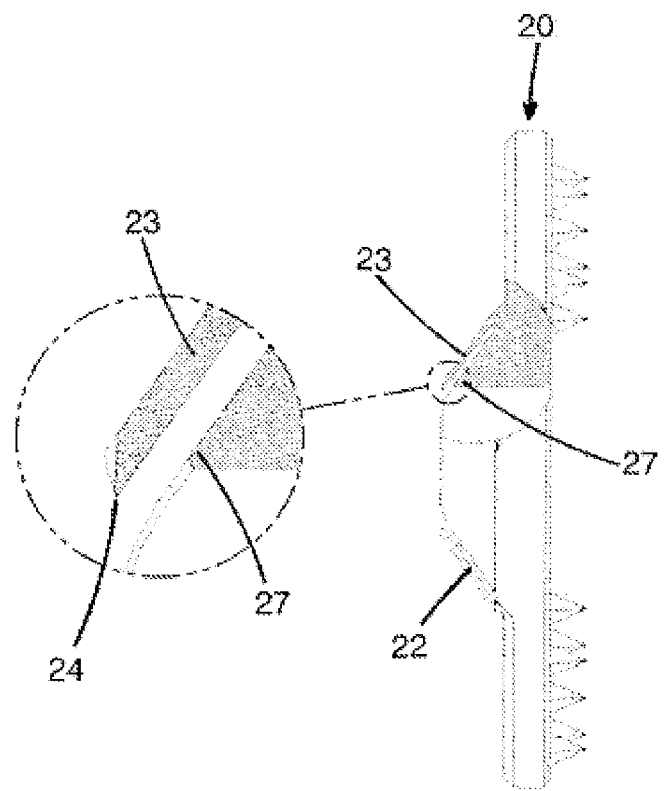
Figure 4:
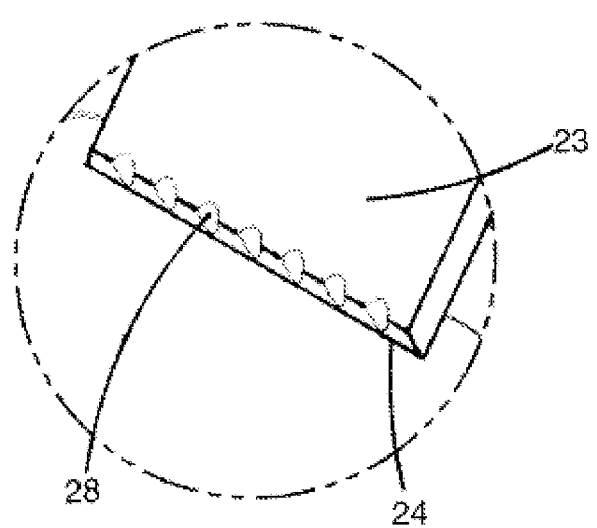
Figure 5:
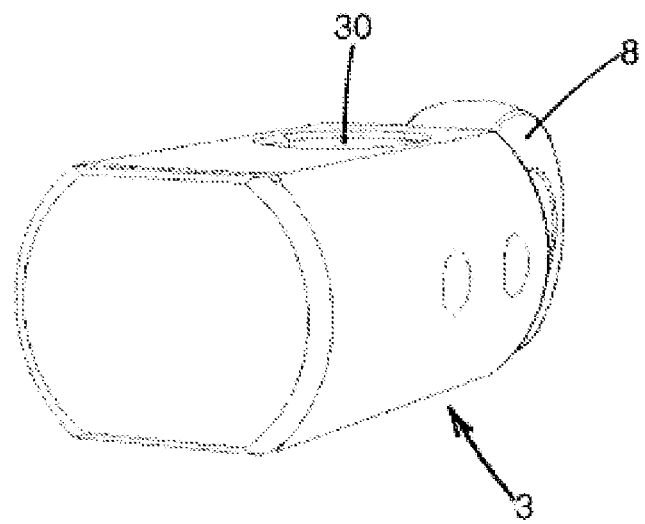
Figure 6:
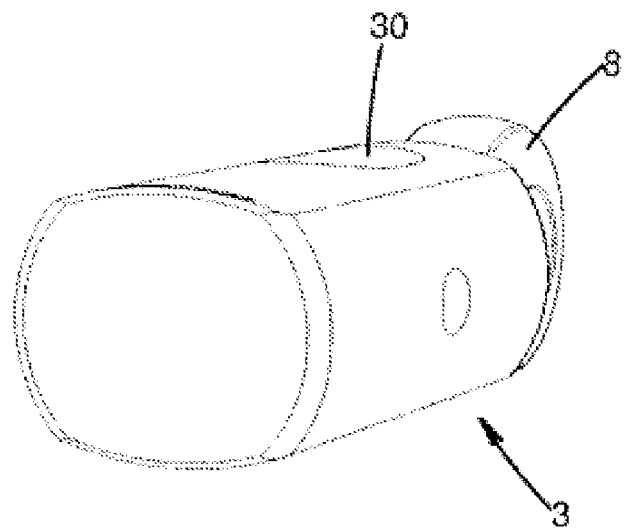
Figure 7:
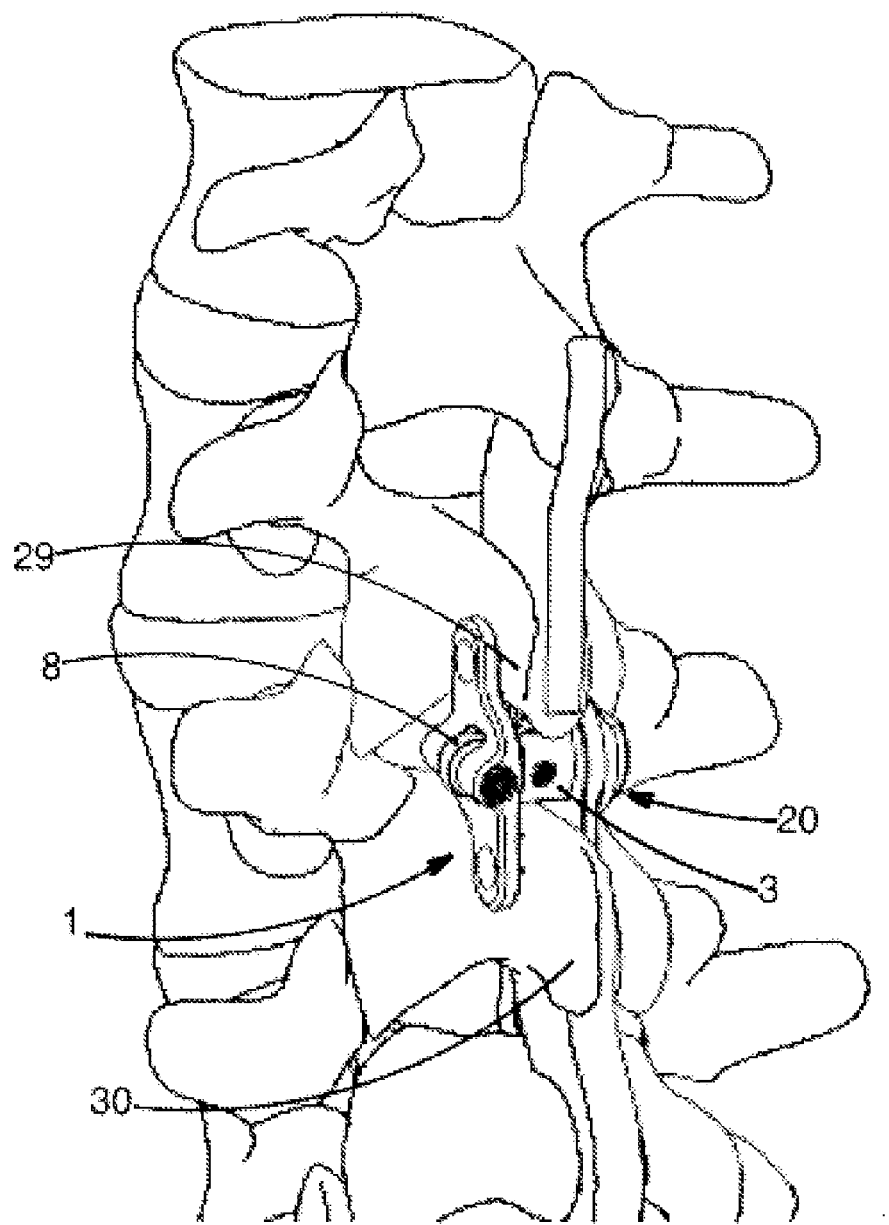
Figure 8:
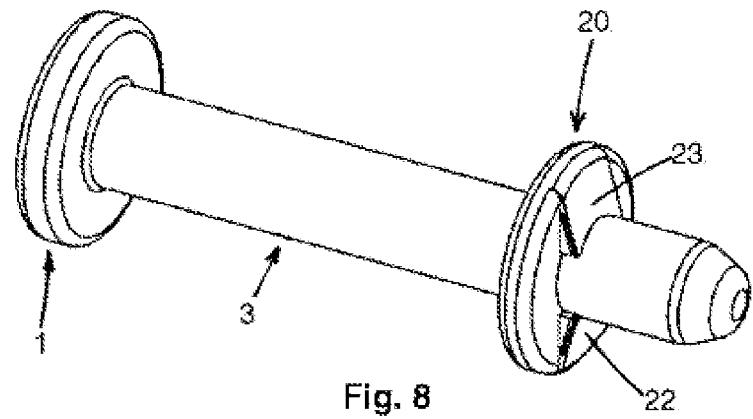
Figure 9:
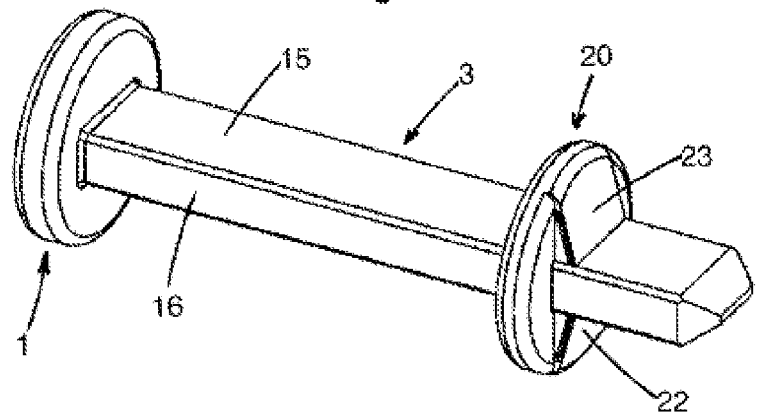
Figure 10:
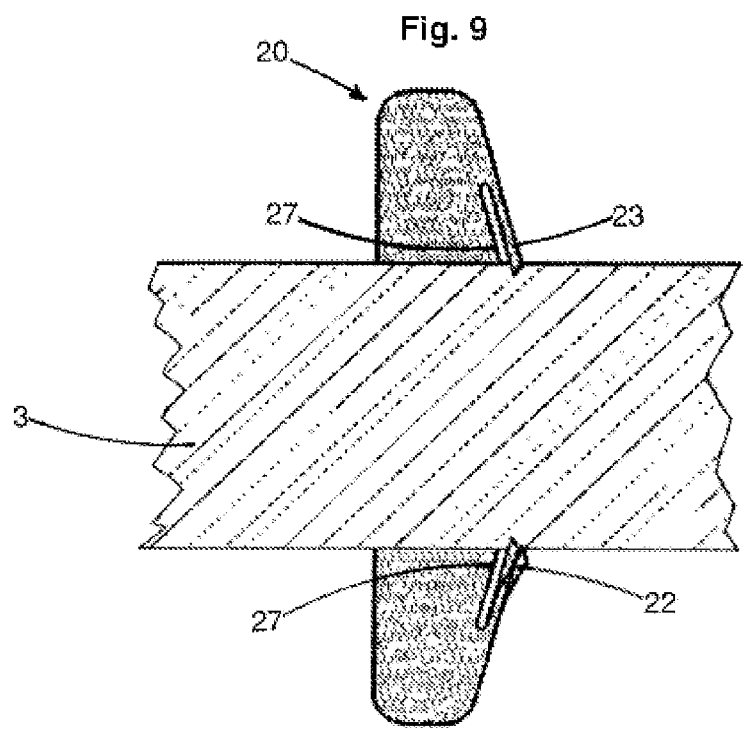

The invention will be better understood by reference to the attached drawings, in which FIG. 1 shows a perspective view of a system for clamping spinous processes according to the invention, the components of which system are shown disassembled, FIG. 2 shows such a system in a functional position, seen in lateral elevation, FIG. 3 shows a side view of a second plate according to the invention, with an enlarged detail illustrating the sharp edge of a flexible and resilient blade provided with notches, and also an abutment, FIG. 4 shows an enlarged detail illustrating the sharp edge of a flexible and resilient blade provided with notches, seen in perspective, FIGS. 5 and 6 each show a perspective view of shafts for spinous processes according to the invention, illustrating cross sections of different shapes, FIG. 7 shows a system according to the invention for spinous processes mounted on adjacent spinous processes, FIGS. 8 and 9 each show a perspective view of bone-clamping systems according to the invention, illustrating shafts of small cross section and of different shapes, FIG. 10 shows a diametrical cross section of a portion of the bone-clamping system from FIG. 8, at the middle of the blades.

In FIG. 1, a first plate 1 of elongate shape is seen on the left. The inner face 2 of this plate 1 is directed toward the shaft 3, constitutes the general plane of the plate and is provided with raised roughening features 6 at its first end 4 and its second end 5. These roughening features 6 are able to embed themselves in spinous processes, as will be seen below with reference to FIG. 7. The shaft 3 has a rounded rectangular cross section and is solid. It comprises, at its first end 7, a circular opening which is arranged diametrically with respect to the axis of the shaft and which is a ring 8 comprising a hole 9. This ring 8 can engage in a cavity 10 provided in the first plate. This cavity 10 has a size that permits the pivoting of the shaft (from the top downward, and vice versa, in this figure). To secure the shaft 3 to the first plate 1, a threaded pin is provided which is screwed into the threaded channel 12, provided in a hump formed on the first plate 1, in order to pass through the hole 9 of the ring 8 and block the translational movements of the shaft 3 with respect to the first plate 1, while at the same time allowing it to pivot. The threaded pin 11 comprises a threaded zone 13 and, toward its center, a spherical hump 14 with a diameter scarcely smaller than the diameter of the hole 9. Thus, the plate 1 is multiaxial, since it is articulated in numerous directions about the axis 11, by virtue in particular of the spherical hump 14.

The upper and lower surfaces 15 and lateral surfaces 16 of this shaft 3 are substantially smooth.

The system also comprises a second plate 20, having a structure comparable to the first plate as regards the plate itself. However, a well 21 is provided at the center of the plate. This well has a shape complementing that of the shaft 3. Two blades 22, 23, each having a sharp end edge 24 in the form of a cutting blade, are fixed to the second plate 20. The sharp end edges 24 extend into the well 21. Thus, when the shaft 3 is introduced into the well 21, the shaft 3 comes into contact with the sharp end edges 24 and a force is necessary to go farther, since the blades 22, 23 scrape the upper and lower surfaces 15.

The blades 22, 23 are fixed via their base to the second plate 20, and their end with the sharp edge 24 is free. Thus, these blades 22, 23 are flexible.

The blades 22, 23 have dimensions (length, width and thickness) which allow them to be sufficiently flexible. They have on this model an inclination of 25° with respect to the general plane of the second plate 20, which allows them to slide in the sense of compression along the shaft 3 and to fasten themselves immediately in the material of the shaft 3 when the movement is reversed. The blades 22, 23 have a sufficient stiffness, depending on their material, thickness and length, which ensures firm contact against the smooth surfaces 15 of the shaft 3.

The sharp end edges 24 of the blades 22, 23 are directed toward the inside of the well. These sharp edges 24 can cooperate with the upper and lower surfaces 15 of the shaft 3 in order to make the coming-together movement of the first plate and second plate 20 irreversible. Indeed, in view of the difference in hardness between the blades and the shaft 3, the sharp edges 24 penetrate slightly into the shaft 3 in order to block any retreat of the second plate with respect to the shaft 3. In the case not shown where the difference in hardness between the blades and the shaft 3 is inverted or whether there is no difference in hardness between the blades and the shaft 3, the sharp edges 24 do not penetrate into the shaft 3 but remain at the surface.

The well 21 has a shape complementing that of the shaft 3, which prevents the relative rotation of the second plate 20 with respect to the shaft 3.

When the second plate is installed and pushed toward the first plate, which can be done with the aid of forceps, the flexible blades move apart and then scrape along the upper and lower surfaces 15 of the shaft 3 and block themselves in place when pushing is stopped. If one tries to push the second plate 20 back, the fact that the sharp edges 24 are blocked means that the blades 22, 23 have a tendency to flatten themselves with respect to the plane of the second plate 20, which further clamps the blades against the shaft 3. Abutments 27 are provided to limit this effect, as will be better seen below.

The shaft 3 is provided with a recess 30, which passes through the shaft 3 and allows bone marrow grafts to be fitted.

In FIG. 2, the system is assembled with a view to being used to clamp objects such as the spinous processes.

The ring 8 has been introduced into the cavity 10, then rigidly connected to the first plate 1 with the aid of the partially threaded pin 11. The pin 11 is provided with a hexagonal socket for screwing with an Allen key. The two plates 1, 20 are shown in parallel, but the first plate 1, on the left-hand side, is able to pivot, for example, in order to better adapt to spinous processes of different thicknesses and of random shapes. A groove 25 can also be seen formed around the end of the shaft 3 away from the ring 8. This groove can permit pre-assembly of the second plate 20 on the shaft 3 by cooperating with the blades 22, 23.

In FIG. 3, which shows an enlarged detail from FIG. 2, the distal end of a blade 23, and the sharp edge 24 thereof, can be better seen. An abutment 27 can also be better seen, which is provided in order to limit the rotation of the blade when a force is exerted to move the two plates 1, 20 away from each other.

FIG. 4 shows an enlarged detail similar to that of FIG. 3, but showing a blade seen in perspective in order to illustrate the series of notches 28 improving the initial fastening of the blades.

FIG. 5 shows a perspective view of a shaft 3 according to the invention, illustrating a cross section of non-circular shape. The cross section is a rounded rectangular shape. In FIG. 6, the short and long sides of a rectangle are replaced by arcs of a circle, with different radii between the short and long sides, measuring respectively 5.2 mm and 71.7 mm.

FIG. 7 shows the assembly of a system according to the invention on adjacent spinous processes 29, 30. Installation even without forceps is easy using one hand. It suffices to obtain the pre-assembled system, the free ends of the blades 22, 23 being inserted into the groove 25, then for example to place a thumb on the first plate 1 and an index finger and middle finger on the wings of the second plate 20, then to press. The shaft 3 passing into the well 21 of the second plate 20 then passes through the latter, and the whole assembly finds itself blocked by the sharp edges 24 of the blades 22, 23.

All sorts of objects, for example the ends of straps, can easily be rigidly connected in the same way. For this purpose, it is also possible to use just one side of the device.

In FIG. 8 and FIG. 9, the same elements are shown, namely, on the left, a first plate 1 with a circular shape instead of being elongate as before. The shaft 3 has a circular cross section in FIG. 8 and a rectangular cross section in FIG. 9 and is solid. The upper and lower surfaces 15 and lateral surfaces 16 of this shaft 3 are plane and substantially smooth for the device in FIG. 9. The end of the shaft 3, to the right, directed away from the first plate 1, is relatively pointed, which can make it easier to join the elements 3 and 20 together.

The system also comprises a second plate 20 of circular shape, having a structure comparable to the first plate 1 as regards the plate itself. However, a well is provided at the center of this plate. This well has a shape complementing that of the shaft 3. Two blades 22, 23, each having a sharp end edge in the form of a cutting blade, are fixed by their bases to the second plate 20. Abutments 27, more clearly seen in FIG. 10, are provided as before, especially since the inclination of the blades 22, 23 is 65° and approaches the vertical to the shaft 3, which makes the presence of an abutment preferable. It should be noted that, in this type of system, the first plate 1 can have a structure comparable to that of the second plate 20 of circular shape. Thus, the two plates can be movable.

The blades 22, 23 and the abutments 27 are better seen in FIG. 10. Two positions of the lower blade 22 can be seen, namely, on the right-hand side, an inclined position when the shaft is introduced and pushed (toward the right), and, on the left-hand side, a straightened position when the device is in place and the blade 22 is engaged in the shaft 3 made of less hard material.

The invention claimed is:

1. A bone-clamping system, comprising:
a shaft with a smooth surface portion parallel to an axis of the shaft;
a first plate attached to the shaft; and
a second plate that is movable and comprises a unidirectional lock with flexible blades with end edges that slide across the smooth surface portion of the shaft when the first and second plates are urged together and that penetrate or bear against the smooth surface portion of the shaft when the first and second plates are urged apart to provide a continuous self-blocking system during a movement of the second plate toward the first plate to block the second plate on the shaft and prevent the first and second plates from moving away from each other.

2. The bone-clamping system as claimed in claim 1, wherein the first and second plates are installed face to face, and the shaft is approximately perpendicular to the first and second plates and passes at least partially through one of the first and second plates,
wherein the first and second plates each comprise an inner face and an outer face, and the first plate is movable relative to the second plate, and the first plate is fixed in translation with respect to the shaft,
wherein the unidirectional lock includes the shaft and the second plate and the flexible blades and does not include either a pawl or a ratchet,
wherein the flexible blades are installed on the second plate and form an angle of 10 to 90° with respect to the axis of the shaft, the end edge of each of the flexible blades bearing against a respective part of the smooth surface portion of the shaft, and
wherein a material of the flexible blades has a hardness identical to or harder than a material of the smooth surface portion of the shaft so that a coming-together of the first and second plates is irreversible without an external aid.

3. The bone-clamping system as claimed in claim 1, wherein the first plate and the second plate are elongate plates adapted to spinous processes.

4. The bone-clamping system as claimed in claim 1, wherein the first plate and the shaft are two separate components, which are coupled in order to permit articulation of the first plate with respect to the shaft.

5. The bone-clamping system as claimed in claim 1, wherein a material of the flexible blades is harder than a material of the smooth surface portion of the shaft.

6. The bone-clamping system as claimed in claim 1, wherein an inclination of one of the flexible blades with respect to a general plane of the second plate is from 10 to 90°.

7. The bone-clamping system as claimed in claim 1, further comprising an abutment opposite and separate from one of the flexible blades that prevents return of the one flexible blade under action of a force tending to move the first and second plates away from each other.

8. The bone-clamping system as claimed in claim 1, wherein one of the flexible blades is provided on each of respective opposing parts of the smooth surface portion of the shaft.

9. The bone-clamping system as claimed in claim 1, wherein surfaces of inner faces of the first and second plates have raised roughening features.

10. The bone-clamping system as claimed in claim 1, wherein a cross section of the shaft has a non-circular shape.

11. The bone-clamping system as claimed in claim 1, wherein the end edges of the flexible blades penetrate the smooth surface portion of the shaft when the first and second plates are urged apart.

* * * * *